US00PP18499P3

(12) United States Plant Patent
Olesen

(10) Patent No.: US PP18,499 P3
(45) Date of Patent: Feb. 19, 2008

(54) FLORIBUNDA ROSE PLANT NAMED 'POULCAS025'

(50) Latin Name: ***Rosa* hybrid**
Varietal Denomination: Poulcas025

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 152 days.

(21) Appl. No.: 11/360,379

(22) Filed: Feb. 22, 2006

(65) Prior Publication Data

US 2007/0199114 P1 Aug. 23, 2007

(51) Int. Cl.
*A01H 5/00* (2006.01)

(52) U.S. Cl. ..... Plt./145

(58) Field of Classification Search ..... Plt./145, Plt./104, 134
See application file for complete search history.

*Primary Examiner*—Kent Bell
*Assistant Examiner*—June Hwu

(57) ABSTRACT

A new garden rose plant of the floribunda class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas025'.

SUMMARY OF THE INVENTION

The present invention constitutes a new and distinct variety of garden rose plant which originated from a controlled crossing between the female seed parent, an unnamed seedling, and the pollen parent 'Poulskov', U.S. Plant Pat. No. 9,062.

The two parents were crossed during the summer of 1996 and the resulting seeds were planted in a controlled environment in Fredensborg, Denmark. The new variety, named 'Poulcas025', originated as a single seedling from the stated cross.

The new variety may be distinguished from its female seed parent by the following combination of characteristics, primarily by flower color. The claimed plant has flowers which are a lighter shade of yellow than the seed parent. Additionally, the claimed plant is taller in growth height than the seed parent variety.

The new variety may be distinguished from its male pollen parent primarily by flower color. The claimed plant has yellow flowers. The pollen parent has pink flowers.

The objective of the hybridization of this rose variety was to create a new and distinct variety for garden use with unique qualities, such as:

1. Uniform and abundant yellow flowers;
2. Vigorous, but uniform and compact growth when propagated both as a budded rose and on its own roots;
3. Exceptional disease resistance;
4. Suitability for small container cultivation.

This combination of qualities is not present in previously available commercial cultivars of this type, known to the inventor, and distinguish 'Poulcas025' from all other varieties of which we are aware.

As part of the rose development program, Mogens N. Olesen germinated the seeds from the aforementioned hybridization during winter of 1996 and conducted evaluations on the resulting seedlings in a controlled environment in Fredensborg, Denmark. 'Poulcas025' was selected in the spring of 1997 by the inventor as a single plant from the progeny of the aforementioned hybridization.

Asexual reproduction of 'Poulcas025' by traditional budding and rooted cuttings was first done by Mogens N. Olesen in the nursery in Fredensborg, Denmark in July, 1997. This initial and other subsequent asexual propagations conducted in controlled environments have demonstrated that the characteristics of 'Poulcas025' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas025'. Specifically illustrated in the drawing are:

FIG. 1.1; Open flower, detached;

FIG. 1.2; Cluster of flower buds at various stages of opening, showing branching, and the attachment of leaves, buds, and peduncles.

FIG. 1.3; Bare stem;

FIG. 1.4; Mature leaf;

FIG. 1.5; Juvenile growth;

FIG. 2.1; Open flowers;

FIG. 2.2; Petals, detached; and

FIG. 2.3; Sepals, pedicels, receptacle with petals removed, showing flower reproductive parts.

DETAILED DESCRIPTION OF THE VARIETY

The following is a description of 'Poulcas025', as observed in its growth in a field nursery in Jackson County, Oreg. Observed plants are 3 years of age, and were grown on *Rosa multiflora* understock. Color references are made using The Royal Horticultural Society (London, England)

Colour Chart, 2001, except where common terms of color are used.

For a comparison, several physical characteristics of the rose variety 'Poulreb', U.S. Plant Pat. No. 12,534, are compared to 'Poulcas025' in Chart 1.

CHART 1

| | 'Poulcas025' | 'Poulreb' |
|---|---|---|
| Petal Count | 25, of which 4 are petaloids | 65 to 75 |
| Flower Diameter | 60 mm | 70 to 80 mm |
| Color, upper petal surface, upon opening. | Yellow Group 5D at margins, blending with Yellow 5B at the middle zone and basal zone | Yellow Group 7B at base, Yellow Group 9D at apex |

FLOWER AND FLOWER BUD

Blooming habit: Continuous.

Flower bud:

*Size.*—Upon opening, 20 mm in length from base of receptacle to end of bud. Bud diameter is 11 mm.

*Bud form.*—Broad based ovoid.

*Bud color.*—As sepals unfold, petals are Yellow Group 4C.

*Sepal inner surface.*—Color: Green Group 137A. Surface: Weak pubescence observed.

*Sepal outer surface.*—Color: Yellow-Green Group 146A. Texture: Smooth with few stipitate glands.

*Sepal shape.*—Apex: Cirrhose. Base: Flat at union with receptacle.

*Sepal margin.*—Margins have medium to weak foliaceous appendages on three of the five sepals.

*Sepal size.*—25 mm long by 7 mm wide.

*Receptacle.*—Texture: Smooth. Shape: Funnel shaped. Size: 7 mm long by 5 mm wide. Color: Yellow-Green Group 144A.

*Peduncle.*—Length: 10 to 14 cm. Diameter: Normally 3 mm. Color: Yellow-Green Group 146B.

*Pedicel.*—Surface: Slightly rough with stipitate glands. Length: 40 to 45 mm on average. Diameter: 2.30 mm on average. Color: Yellow-Green Group 144A to 146B. Strength: Medium.

Flower bud development: Flower buds are normally borne in clusters of 5 flower buds per stem. Inflorescence type is a panicle.

Flower bloom:

*Fragrance.*—Medium floral scent.

*Duration.*—The blooms have a duration on the plant of up to 10 days. Petals fall cleanly away from plant after flowers have fully matured.

*Size.*—Flower diameter is 60 mm when open. Flower depth is 35 mm.

*Flower shape.*—General shape is an open cup, double flower, with petals that curve out from the center.

*Shape of flower, side view.*—Upon opening the upper portion is flat. The lower portion is flat. After opening, the upper portion is flattened convex. The lower portion is concave.

Petalage: Under normal conditions, flowers have 25 petals total, 4 of which are petaloids.

Petal color:

*Upon opening, outer petals.*—Upper surface: Yellow Group 5D at marginal zone blending with Yellow Group 5B at middle zone and basal zone. Lower surface: Yellow Group 8D at marginal zone blending with Yellow Group 9C at middle to basal zone.

*Upon opening, inner petals.*—Upper surface: Yellow Group 9B with light intonations of Yellow Group 4C at the apex. The margins show light intonations of Orange Group 26B. Lower surface: Yellow Group 9B to 9C. Margins show intonations of Orange Group 29A to Orange Group 26B.

*Basal petal spots, upon opening.*—No distinctive coloration at the petal base observed.

*After opening, outer petals.*—Upper surface: Marginal zone Yellow Group 4D. Middle zone yellow Group 8B and 8C. Basal zone Yellow Group 9B. Lower surface: Marginal zone Yellow Group 4D. Middle zone Yellow Group 8C and basal zone Yellow Group 9B to 9C.

*After opening, inner petals.*—Upper surface: Marginal zone Yellow Group 11B to 11C with intonations of Yellow Group 4D. Middle zone Yellow Group 11A. Basal zone is Yellow Group 9A. Lower surface: Yellow Group 11B.

*Basal petal spots, after opening.*—No distinctive coloration at the petal base observed.

General tonality: On open flower Yellow Group 4B at center with Yellow Group 4D at the periphery. Afterwards, general tonality is Yellow Group 10C with White Group 155B to Yellow Group 11D at the periphery.

Petals:

*Petal reflex.*—Somewhat reflexed.

*Margin.*—Entire and uniform.

*Shape.*—Generally elliptic. Apex shape: Rounded. Base shape: Obtuse.

*Size.*—Outer petals: 24 mm (l)×26 mm (w). Inner petals: 16 mm (l)×16 mm (w).

*Texture.*—Smooth.

*Thickness.*—Thin.

*Arrangement.*—Not Formal.

Petaloids:

*Quantity.*—4 on average.

*Shape.*—Elliptical with acute base.

*Color.*—Upper surface: Yellow Group 9B with light intonations of Yellow Group 4C at the apex. The margins show light intonations of Orange Group 26B. Lower surface: Yellow Group 9B to 9C. Margins show Orange Group 29A to Orange Group 26B. Size: 14 mm long×11 mm wide.

Reproductive organs:

*Pollen.*—None observed.

*Anthers.*—Size: 2.5 mm average length. Color: Yellow-Orange Group 22A. Quantity: 90 to 100.

*Filaments.*—Color: Yellow Group 8A. Length: Normally 4 mm.

*Pistils.*—Length: Normally 9 mm. Quantity: 75 to 85.

*Stigmas.*—Superior in location relative to the length of the filaments and the height of the anthers. Color: Yellow-Green Group 144C.

*Styles.*—Color: Yellow-Green Group 144C.

*Hips.*—None Observed in the field nursery in Jackson County Oreg.

PLANT

Plant growth: Moderately compact, upright and bushy. When grown as a budded field grown plant on *Rosa multiflora* understock, the average height of the plant is 35 cm and the average width is 30 cm.

Stems:

*Color.*—Juvenile growth: Yellow-Green Group 146A. Mature growth: Yellow-Green Group 146B.

*Length.*—On average, canes are 18 cm from the base of the plant to the flowering portion.

*Diameter.*—Normally 4.5 mm.

*Internodes.*—On mature canes, there is an average distance of 25 to 30 mm between nodes.

*Surface texture.*—Young wood: Smooth. Older wood: Smooth.

Prickles:

*Incidence.*—10 prickles per 10 cm of stem.

*Size.*—Average length of prickles on mature stems is 6 mm.

*Shape.*—Upper side: Convex. Lower side: Concave.

*Color.*—Juvenile prickles: Greyed-Red Group 181B to 181C. Mature prickles: Greyed-Yellow Group 160A.

Plant foliage: Normal number of leaflets leaves in middle of the stem: 5 leaflets.

*Compound leaf.*—90 to 110 mm (l)×55 to 90 (w).

*Quantity.*—3 leaves per 10 cm of stem on average.

*Color of mature foliage.*—Upper side: Yellow-Green Group 146A to 147A. Lower side: Yellow-Green Group 146B.

*Color of juvenile foliage.*—Upper side: Yellow-Green Group 144A. Lower side: Yellow-Green Group 144A. Anthocyanin: Greyed-Orange Group 176A at the margins.

Plant leaves and leaflets:

*Stipules.*—Size: 9 to 13 mm in length. Shape: Linear, slightly broad based with fine outward extending apecies. Margins: Finely serrated with many stipitate glands. Color: Yellow-Green Group 144A.

*Petiole.*—Length: 22 to 25 mm. Diameter: Normally 1.25 mm.

*Upper surface.*—Color: Yellow-Green Group 146A with anthocyanic pigments of Greyed-Purple Group 183C. Observations: Stipitate glands.

*Lower surface.*—Color: Yellow-Green Group 144B. Observations: Small prickles.

*Rachis.*—Length: 30 to 40 mm. Upper surface: Color: Yellow-Green 146A with anthocyanic pigments of Greyed-Purple 183C.

*Lower surface.*—Color: Yellow-Green 144B. Observations: Small prickles observed.

*Leaflet.*—Edge: Doubly serrated. Size: Average size of the terminal leaflet on normal leaves is 32 to 45 mm in length by 28 to 34 mm wide. Shape: Elliptical. Base: Cordate. Apex: Acuminate. Texture: Smooth. Thickness: Average. Arrangement: Odd pinnate. Venation: Reticulate. Glossiness: Slightly Glossy.

Disease resistance: Above average resistance to powdery and downy mildew, rust, black spot, and *Botrytis* under normal growing conditions in Jackson County, Oreg.

Cold hardiness: The variety is tolerant to USDA Cold Hardiness Zone 6.

It is claimed:

1. A new and distinct variety of rose plant of the floribunda rose class named 'Poulcas025', substantially as illustrated and described herein, due to its abundant yellow flowers, disease resistance, and extended period of bloom.

* * * * *

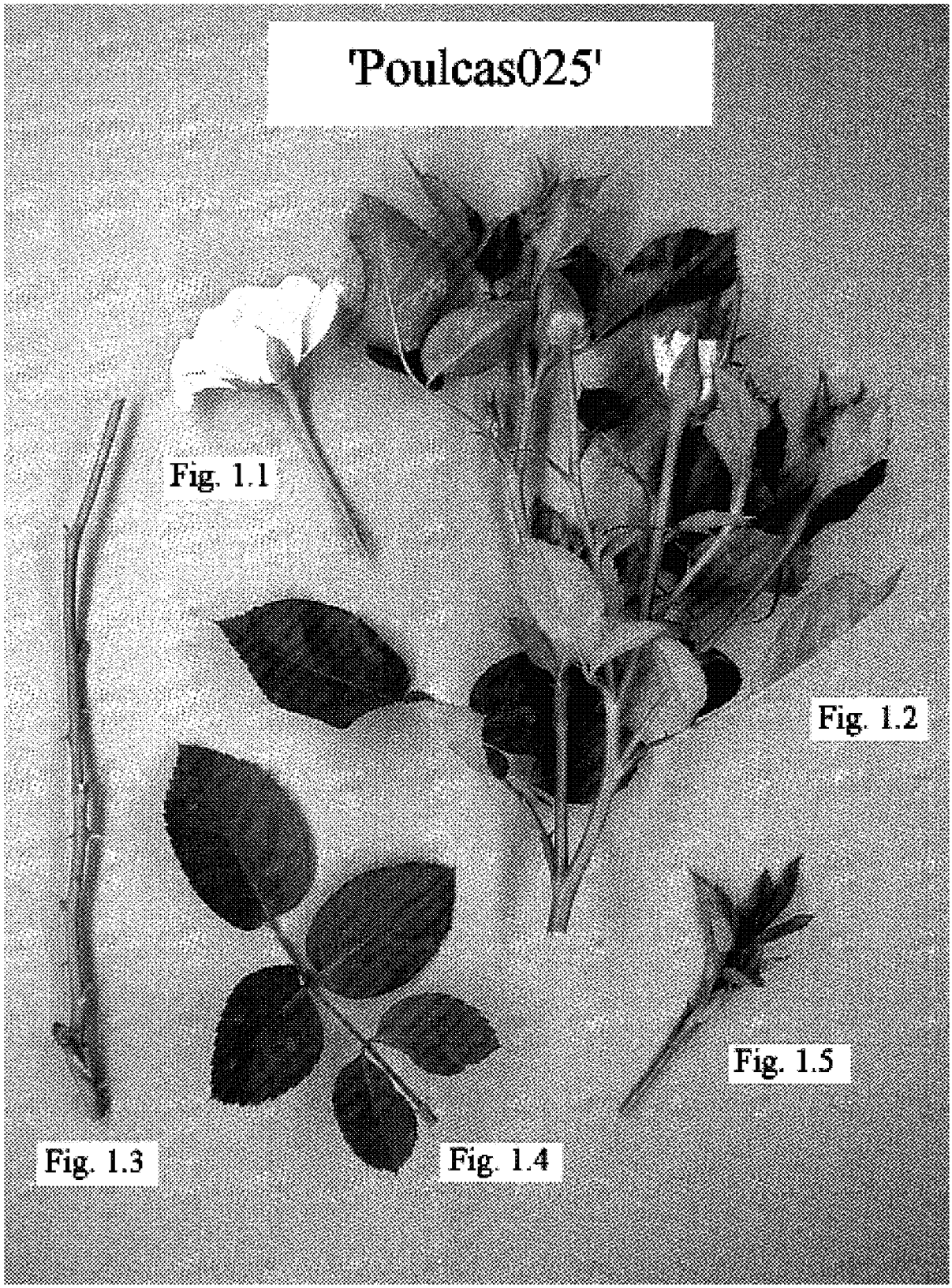
'Poulcas025'
Fig. 1.1
Fig. 1.2
Fig. 1.3
Fig. 1.4
Fig. 1.5

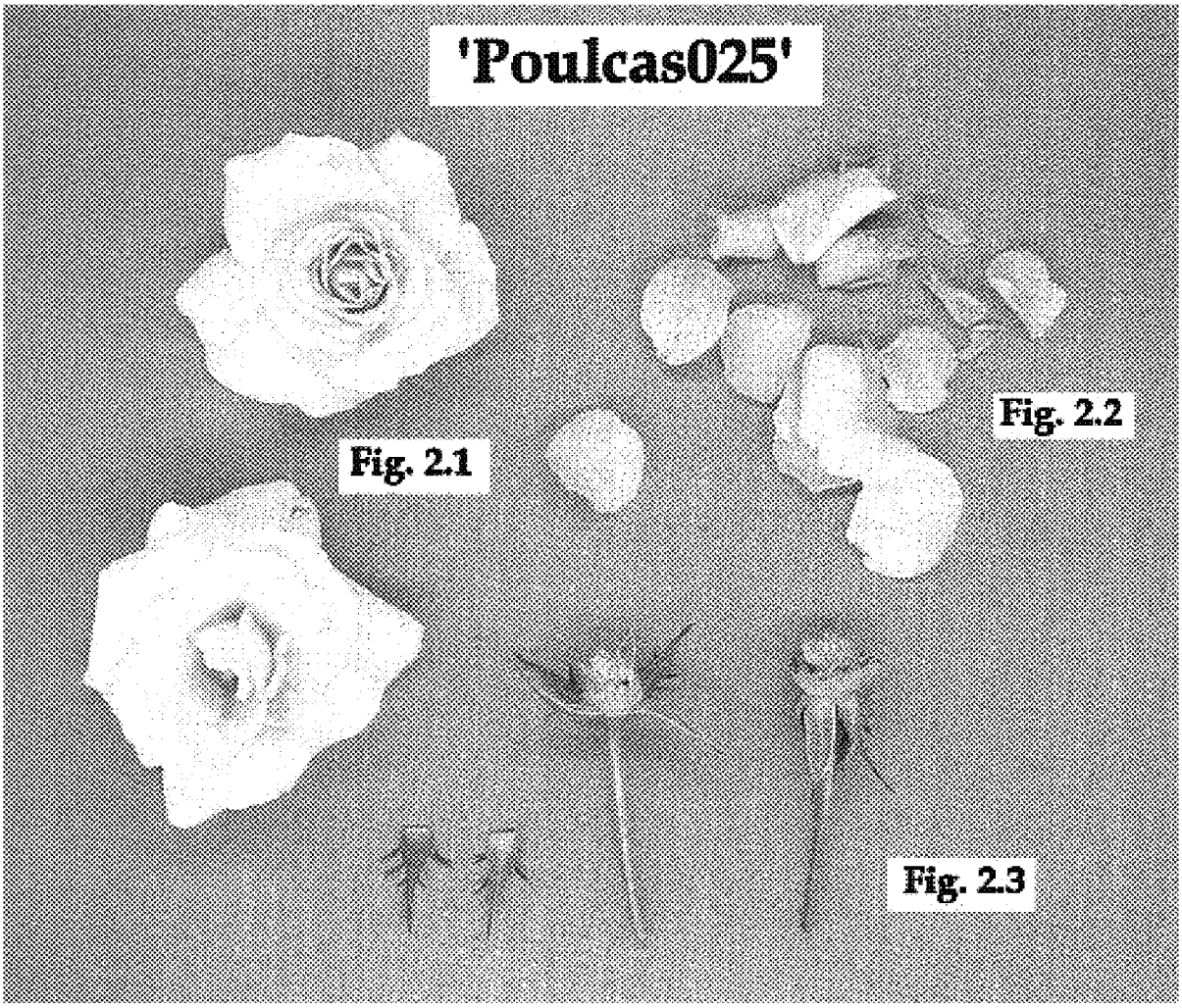
'Poulcas025'
Fig. 2.1
Fig. 2.2
Fig. 2.3